(12) United States Patent
Baker

(10) Patent No.: US 6,229,957 B1
(45) Date of Patent: May 8, 2001

(54) PHYSIOLOGICAL FLUID WARMING PROCESS AND APPARATUS

(76) Inventor: Joseph Baker, 73 Fairview East, Tequesta, FL (US) 33469

( * ) Notice: Subject to any disclaimer, the term of this patent is extended or adjusted under 35 U.S.C. 154(b) by 0 days.

(21) Appl. No.: 09/312,459

(22) Filed: May 14, 1999

(51) Int. Cl.[7] .............................. F24H 1/00; A61M 5/00
(52) U.S. Cl. ........................ 392/470; 219/501; 219/482; 604/114
(58) Field of Search ............................ 392/470, 480–481, 392/488; 604/113–114; 219/501, 497, 485, 482

(56) References Cited

U.S. PATENT DOCUMENTS

| | | | |
|---|---|---|---|
| 3,908,652 | * 9/1975 | Weissinger | 392/470 |
| 4,019,020 | 4/1977 | Bilbee et al. . | |
| 4,314,143 | 2/1982 | Bilstad et al. . | |
| 4,523,078 | 6/1985 | Lehmann . | |
| 4,678,460 | 7/1987 | Rosner . | |
| 4,759,749 | 7/1988 | Verkaart . | |
| 4,844,074 | * 7/1989 | Kurucz | 392/470 |
| 4,874,359 | * 10/1989 | White et al. | 604/113 |
| 4,878,537 | 11/1989 | Verkaart . | |
| 4,900,308 | 2/1990 | Verkaart . | |
| 4,906,816 | 3/1990 | van Leardam . | |
| 5,125,069 | 6/1992 | O'Boyle . | |
| 5,250,032 | 10/1993 | Carter et al. . | |
| 5,408,577 | * 4/1995 | Weber, Jr. et al. | 392/480 |
| 5,989,238 | * 11/1999 | Ginsburg | 604/113 |
| 6,037,571 | * 3/2000 | Christopher | 219/482 |

FOREIGN PATENT DOCUMENTS

| | | | |
|---|---|---|---|
| 9007947 | * 7/1990 | (WO) | 604/114 |
| 9938356 | * 7/1999 | (WO) . | |

OTHER PUBLICATIONS

Journal of Trauma, May, 1984; Rapid vol. Replacement for Hypovolemic Shock.
Journal of Trauma, Feb. 1986; Normothermic Rapid vol. replacement For Hypovolemic Shock.
Anaesthesia, 1990; An Evaluation of the Level 1 Blood Warmer Series.
Anesthesiology, Laboratory report, Nov. 1992; A Comparative Study of Blood Warmer Performance.
Critical Dare Medicine, Jul., 1995; In–Line Microwave Blood Warming of In–Date Human Packed Red Blood Cells.

* cited by examiner

Primary Examiner—John A. Jeffery
(74) Attorney, Agent, or Firm—McHale & Slavin

(57) ABSTRACT

The present invention provides both a process and apparatus for rapidly warming and delivering relatively high volumes of a physiological fluid. Unique to this invention is the ability to warm and infuse physiological fluids at a rate of up to about 1000 ml/min without causing damage to the fluid components, e.g. lysing or rupture of cells, or upsetting the normothermic equilibrium of the patient. Further unique to this invention is the utilization of a 12 VDC source, e.g. a battery source, as an amperage supplement to be used simultaneously with an AC power source, thereby enabling the heating of physiological fluids at a rate which surpasses that normally attainable through the sole use of facility provided AC power.

12 Claims, 8 Drawing Sheets

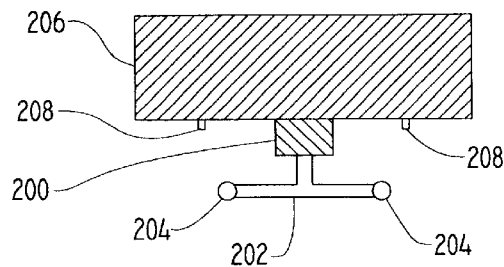
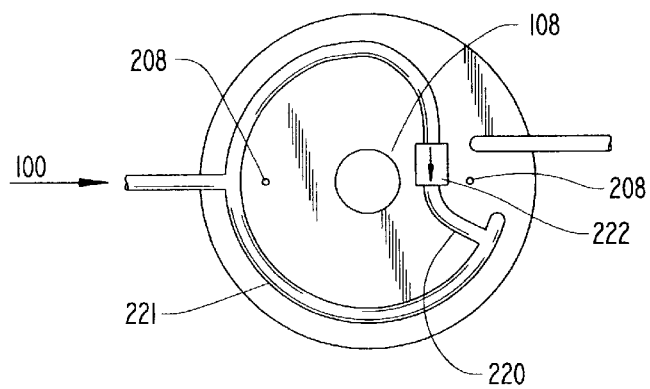
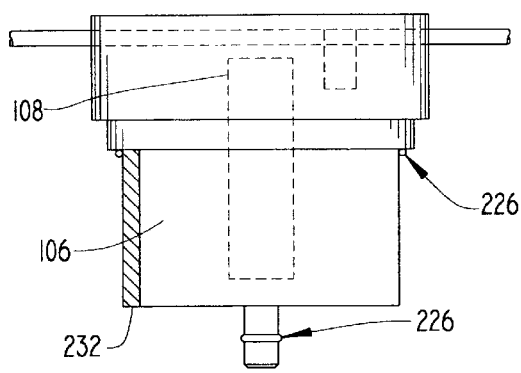
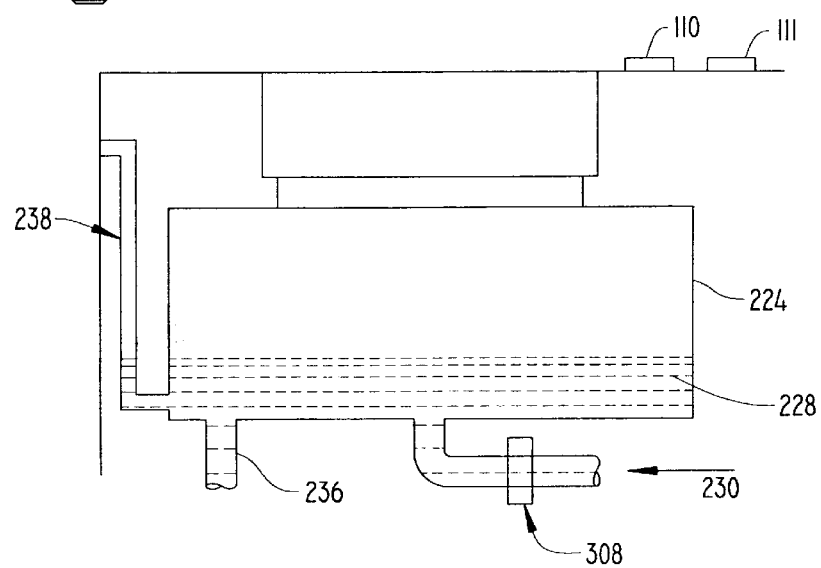

PHYSIOLOGICAL FLUID WARMING PROCESS AND APPARATUS

FIELD OF THE INVENTION

This invention relates to warming devices required for safely warming physiological fluids, inclusive of blood and non-blood related products, prior to their infusion to a patient. The invention specifically relates to a warming device which utilizes both alternating current (AC) and direct current (DC) sources of energy, in concert, to provide for the safe and effective warming at high rates of infusion.

BACKGROUND OF THE INVENTION

The successful resuscitation of patients suffering from hypovolemic shock requires infusion of fluids at a very rapid rate. Hypovolemic shock, which may have been brought on secondary to intraoperative or possibly traumatic hemorrhage, must be treated aggressively by rapid administration of fluids, for example, crystalloids, blood products, colloids and the like. Reductions in physiological markers such as blood pressure, cardiac output and coronary blood flow may often lead to a reduction in tissue perfusion, organ damage, loss of kidney function and acidosis which, if left untreated, can result in physiologic changes which are often irreversible and sometimes fatal. As various products are infused in order to restore normal fluid volumes, it is most important to maintain normothermic conditions so as to avoid the occurrence of transfusion induced hypothermia. Prior artisans have incorporated various types of extracorporeal heat exchangers in an effort to maintain the infusate temperature at required levels, e.g. above about 37° C. at flow rates of about 500 ml/minute, but such devices have proven inadequate to provide the 1000 ml/minute or more which is so often required. It should be understood that correction of this inadequacy is not so simple as resizing of the heater capacity as a function of flow rate and expected temperature change of the fluid. On the contrary, the problem stems from inadequate amperage capacity in existing facilities, making it virtually impossible to achieve the required heating capacity by utilization of facility provided power alone. Additionally, prior art devices have concentrated on the temperature of the infusate at the outlet of the heat exchanger, giving little regard to the heat lost in the connecting tubing which fluidly couples the heat exchanger to the patient. Thus, the infusate temperature, at the point of entry to the patient, is often below nominal design parameters.

While it is known to provide a fluid warming device which is alternatively powered by AC or DC current—in order to facilitate transport of a patient, e.g. from the ER to the operating room—no prior art device teaches or discloses the use of a battery source (DC power) as an amperage supplement to be used simultaneously with an AC power source, thereby enabling the heating of physiological fluids at a rate which surpasses that possible with AC alone.

DESCRIPTION OF THE PRIOR ART

U.S. Pat. No. 4,019,020 discloses an apparatus for maintaining a fluid supply such as human blood at optimum temperatures by utilizing an electrically heated inner mandrel maintained at a thermostatically controlled temperature. The temperature of the mandrel is controlled via thermostats being electrically coupled in series with electrical heaters.

U.S. Pat. No. 4,523,078 discloses a portable electrically heated warming container for heating a plurality of infusion containers within a case. The device includes a provision for detachably connecting the electric heater plug to a rescue vehicle power supply. A further electrical connector permits energization of the heating element from a nonvehicular power supply when removed from the rescue vehicle.

U.S. Pat. No. 4,678,460 discloses a self-contained portable apparatus for the rapid warming and infusion of massive amounts of parenteral fluid into a patient. The associated fluid warming system is a dual heat system, having a primary heating element for maintaining the apparatus in a stand-by condition when the apparatus is not in use, and a secondary heating element for raising the temperature of the fluid to the desired temperature while the apparatus is in use. By operating the secondary heating element only during the time the primary heating element is inoperative and vice-versa, the electrical load on the hospital electrical system can be more easily maintained within the maximum limit without loss in performance of the fluid warming system.

U.S. Pat. No. 5,125,069 discloses a blood warmer for changing the temperature of an infusible fluid from a first temperature to a second predetermined temperature. The assembly includes a thermoelectric heat pump with a slot for releasably receiving a cartridge so that the heat pump engages the wall of the cartridge. An electrical circuit is responsive to a temperature sensor for controlling operation of the heat pump so that the liquid exiting the cartridge is at a predetermined temperature. The device uses an AC rectified power supply to provide suitable DC power for the heat pumps and control circuitry. A battery may be provided and selectively connected by a switch when the warmer is to be used in a portable application, or when the AC power is not available.

U.S. Pat. No. 5,250,032 discloses a heater for warming blood flowing through an intravenous tube prior to its entry into a patient. The heater is housed in an elongated channel which is secured to the arm of the patient. The housing contains a heating element controlled by a control circuit and powered by batteries.

SUMMARY OF THE INVENTION

The present invention provides both a process and apparatus for rapidly warming and delivering relatively high volumes of a physiological fluid. Unique to this invention is the ability to warm and infuse physiological fluids at a rate of about 1000 ml/min, at a controlled temperature range to the patient, e.g. of about 38° C. +/- at least about 0.5° C., preferably +/- about 0.1° C., without causing damage to the fluid components, e.g. lysing or rupture of cells; and without upsetting the normothermic equilibrium of the patient. Physiological fluids used for infusion into the body are often stored under refrigerated conditions to maintain their freshness, e.g. at temperatures of about 4° C. Such fluids may be selected from blood products such as whole blood, packed cells, plasma or the like, along with non-blood products such as colloids and crystalloids, and various mixtures thereof. Prior to infusion, these fluids must be warmed to a temperature which renders them safe for infusion into a living patient without upsetting the normothermic equilibrium and inducing hypothermia. Additionally, when transporting such fluids to the patient, certain flow conditions can cause damage to the fluids at a cellular level, e.g. the inclusion of areas of high pressure drop can induce unwanted turbulence and produce a shearing effect which may be damaging to the blood cells. The instant invention fluidly couples one or more vessels, such as flexible plastic bags, containing one or more of the desired physiological fluids, to an in-line pumping means which may be operated either manually or motor driven or the pump may be selectively disengaged to allow the use of other means for moving the fluid through the system. The pump, e.g. a line pump along with its associated valves and tubing, is designed to provide laminar flow for transport of the physiological fluid to a heat exchanger. The heat exchanger, which in the preferred embodiment is a spirally wound heat exchange element, is of sufficient capacity to raise the temperature of the physiological fluid to the required level at a flow rate which is designed to prevent cell damage. In order to protect the patient, it is known to simultaneously filter the fluid and remove excessive air bubbles. This invention uniquely positions the filter/air separator within the warming bath to avoid temperature losses while carrying out these processes. In order to maintain the desired physiological fluid outlet temperature, at the maximum required flow rates, the instant invention provides heaters which utilize both a facility provided AC source and a built-in supplementary DC source, such as batteries, fuel cells or the like. The AC and DC power sources may be utilized simultaneously if necessary, based upon the demand dictated by the temperature control assembly.

In a particular embodiment, batteries act as a source of DC power which supplements the 112 VAC, providing increased power to the heaters when high fluid volume dictates an increased power demand, and thereby enabling a flow rate of up to 1000 cc/min while maintaining an infusate temperature of about 38° C., +/−0.5° C., preferably +/−0.1° C. In situations where facility provided AC power is either unavailable or inoperative, the system can be operated solely on battery power, and is capable of providing up to 500 cc/min at an infusate temperature of about 38° C.+/−0.1° C. Further unique to this device is a power management module which monitors and maintains the instantaneous battery condition, and further totalizes the number of times the batteries have cycled, so as to warn the operator of an impending need to replace the batteries.

It has further been discovered that the physiological fluid experiences a significant heat loss as it is transported to the patient, e.g. from the associated tubing. Thus, the present invention utilizes insulated transport tubing to maintain the physiological fluid's temperature within a range sufficient to avoid the occurrence of hypothermia induced shock.

The heat exchanger and associated flow control apparatus are supplied in the form of a sterile, sealed, disposable Y-set adapter and heat exchanger assembly designed for simplified plug-in/plug-out installation of all biologically contaminated parts of the system. The Y-set adapter and heat exchanger assembly includes tapping means, e.g. bag spikes as are well-known in the art, designed for easy attachment to one or more vessels containing a physiological fluid to be heated. The tapping means are constructed and arranged to provide for a flow of liquid from the vessels, e.g. collapsible plastic bags, and are fluidly coupled to anti-reversing and non-pinching flow control valves, particularly selected for their low pressure drop characteristics. The inventor has discovered that the employment of valves which pinch the tubing in order to control flow therethrough, cause a residual flow loss and pressure drop when opened, due to the tubing having a "memory" which prevents it from returning to its fully opened position upon release of the valve. Alternative, non-pinching valves, such as gate or ball valves, having essentially no pressure drop, are therefore preferred.

The spirally wound heat exchanger assembly is designed for self-centering plug-in fluid coupling with a source of warming fluid, particularly a reservoir for maintaining a desired volume of warming fluid. The assembly also incorporates means for traversal of the fluid to be heated within said reservoir, and includes integral air venting, fluid filtration and insulated outlet means for directing the warmed physiological fluid to a Y-coupling. The Y-coupling, which is in fluid communication with the heat exchanger assembly, is in turn fluidly connected to one or more insulated fluid conduits, e.g. vacuum or warm-water jacketed insulated tubing, which are each in fluid communication with flow control valves and connectors which ultimately terminate at catheters attached to the patient.

Accordingly, it is an objective of the present invention to provide physiologic fluids to a patient at high rates of infusion while preventing hypothermia and physical damage to the fluids.

It is a further objective of the present invention to provide a system for infusion of physiological fluids which is designed to minimize pressure drop.

It is an additional objective of the present invention to teach a device which provides increased heat transfer capacity for warming physiological fluids exclusive of facility provided AC power.

It is yet another objective of the instant invention to provide a physiological fluid warming device having power management capabilities for controlling the simultaneous utilization of AC and DC power supplies.

It is still a further objective of the instant invention to provide a physiological fluid warming device having safety interlocks and an integral fluid-temperature controller.

It is yet another objective of the instant invention to provide a fluid warming device containing an integral system for monitoring and maintaining battery condition and forecasting the need for battery replacement.

It is still an additional objective of the instant invention to provide a fluid warming device which incorporates insulated transport tubing between the heat exchange assembly and the patient thereby minimizing temperature losses prior to infusion.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 2A is a cross sectional view of the warm water bath cover including the line pump;

FIG. 2B is a top view of the heat exchanger assembly showing the interaction of the line pump and heat exchanger;

FIG. 2C is a cross-sectional side-view of the heat exchanger assembly;

FIG. 2D is a cross-sectional side view of the hot water reservoir;

DETAILED DESCRIPTION OF THE INVENTION

Figure 1:
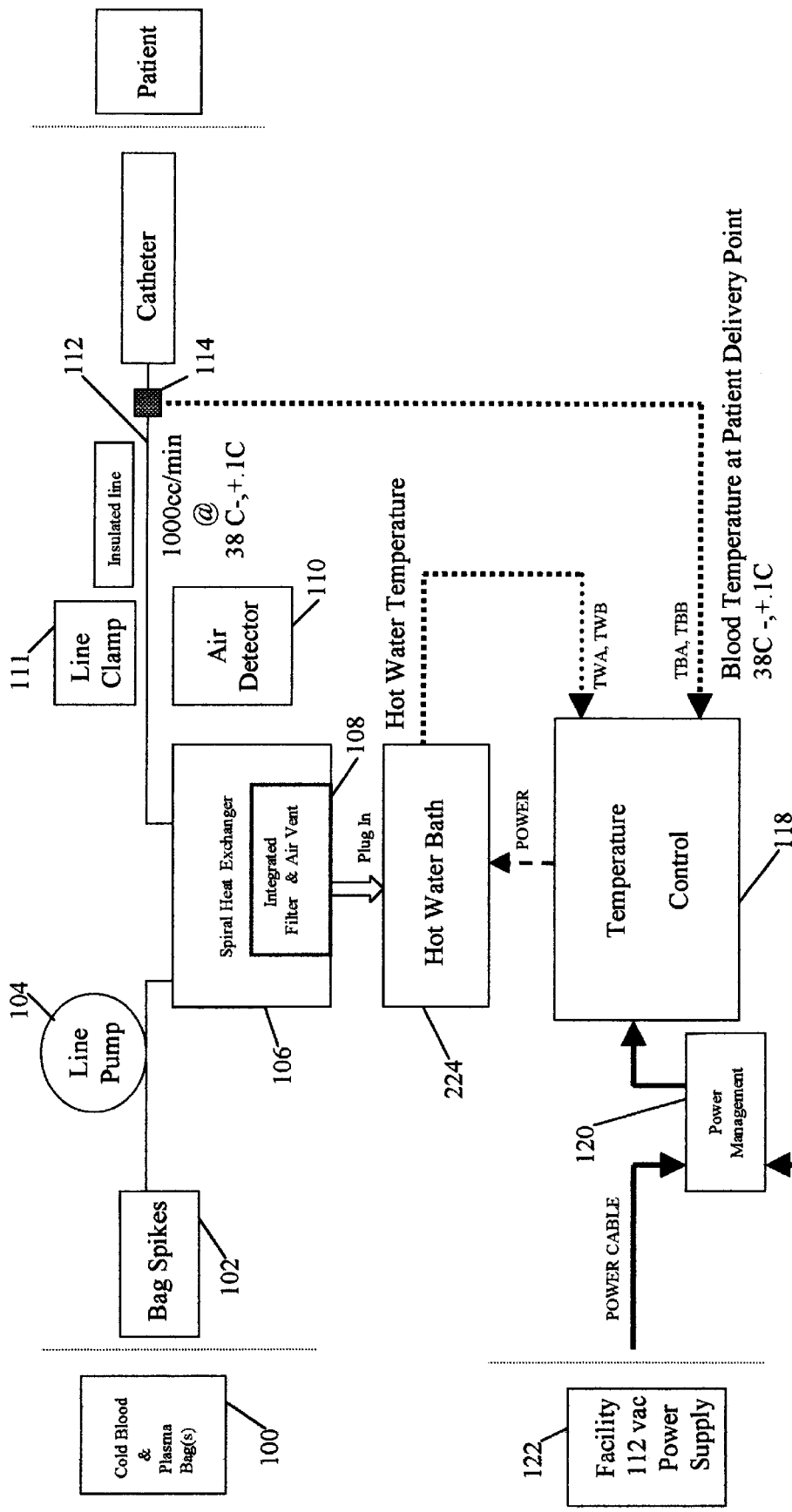
FIG. 1 is a diagrammatic representation of the physiological fluid warming device of the present invention.

Referring to FIG. 1, refrigerated physiological fluids 100 are removed from storage for transfusion to a patient. Typically, these fluids are whole blood, related blood products such as plasma, packed cells, and the like. The fluids are stored at a temperature of about 4° C. and must be warmed to about 38° C. prior to infusion to the patient. The fluids, which are typically stored in collapsible plastic bags, are attached to a means for tapping the fluid contained therein; one or more bag spikes 102 are commonly used for this purpose. The system is designed to have a priming volume of less than 100 ml, preferably in the range of 50–100 ml. The cold fluid 100 is gravity fed into the warming apparatus, at which point the fluid is drawn through the apparatus preferably by the action of a line pump 104, although manual means may be employed, e.g. when conservation of electrical power is necessary. The line pump is a commonly used device for movement of physiological fluids and comprises (see FIG. 2A) a small motor 200 which turns a bar 202 having a roller 204 at each end. As the motor rotates, the rollers squeeze the tubing 221 in a manner such that the fluid is pushed axially through the tubing. Unique to this invention is the incorporation of the line pump 104 into the cover of the warm water bath 206 (as best seen in FIG. 2A) and the inclusion of self-centering devices 208 built into the warm water bath and cover to align the line pump upon closure of the cover 206. The self-centering devices simultaneously align the Y-set plastic line pump bypass line 220 and high pressure relief valve 222 (seen in FIG. 2B) to provide relief of any excessive line pressure. The fluid continues through the circuitous path provided by the spirally wound heat exchanger assembly 106 which contains an integrated physiological fluid filter and air venting assembly 108. The filter is in the range of about 150–175 micron mesh size and the vent will release up to about 500 ml of air per minute. The central location of the assembly 108, within the water bath, eliminates heat loss from the assembly and is further unique to this invention. Having traversed the heat exchanger assembly 106, the fluid continues along the tubing and flows through an air detector 110. The air detector is a non-invasive air/bubble detector designed to surround the flexible tubing and, in a preferred embodiment, utilizes ultrasonic technology to pass high frequency acoustic energy through the fluid flowing within the tubing, thereby detecting the presence of air, air bubbles or foaming. Such a detector is available from Introtek International, L.P. and is useful to detect air bubble volume in a range of about 50–100 microliters within the physiological fluid within a time window. As best seen in FIG. 2D remotely controlled line clamp 111 surrounds the tubing and will halt the flow of fluid through the system upon receipt of a signal from the detector 110 warning of excessive air, e.g. greater than a particular value, for example greater than about 50–100 microliters air bubble volume, in the fluid. The line 112 which carries the warmed fluid to the patient is insulated so as to minimize temperature losses during transport. The particular type of insulation is not critical, so long as it is effective to allow maintenance of the required temperature parameters. The insulated lines contemplated by the invention may be exemplified by, but are not limited to, those lines having fibrous insulative material coatings, vacuum-jacketed lines, warm-water jacketed lines, and warm-air jacketed lines. At high flow rates, e.g. about 1000 ml/min, the system is designed to maintain temperatures at nominal parameters, for example at ranges as fine as about 38° C.+/−0.1° C. The temperature is monitored by a detector 114, which in a preferred embodiment is a dual temperature detector positioned at or about the entry into the catheter, which is in electrical communication with the temperature control system 118. If the fluid temperature falls outside of nominal parameters, then the temperature controller will act to correct this condition. The temperature controller 118 contains heating and pumping means which will be later described in FIG. 6. Dependent upon the flow rate required and the temperature differential which must be satisfied, the power management system 120 will coordinate input from the temperature controller 118 and will utilize a facility supplied AC power supply 122, an integral 12 VDC power source 124, or both.

Referring now to FIGS. 2C and 2D, upon insertion of the plug-in heat exchanger assembly 106, within the warm water reservoir 224, integral seals 226, positioned upon the heat exchanger assembly 106 engage mating surfaces of the warm water reservoir to segregate the warming fluid 228. Hot fluid enters centrally 230, flows through the heat exchanger 106 and exits back into the reservoir 224 at the heat exchanger outlet 232, for recirculation and reheating via line 236. A water level indicator 238 is provided so that the technician may easily determine when additional water is required.

Figure 3:
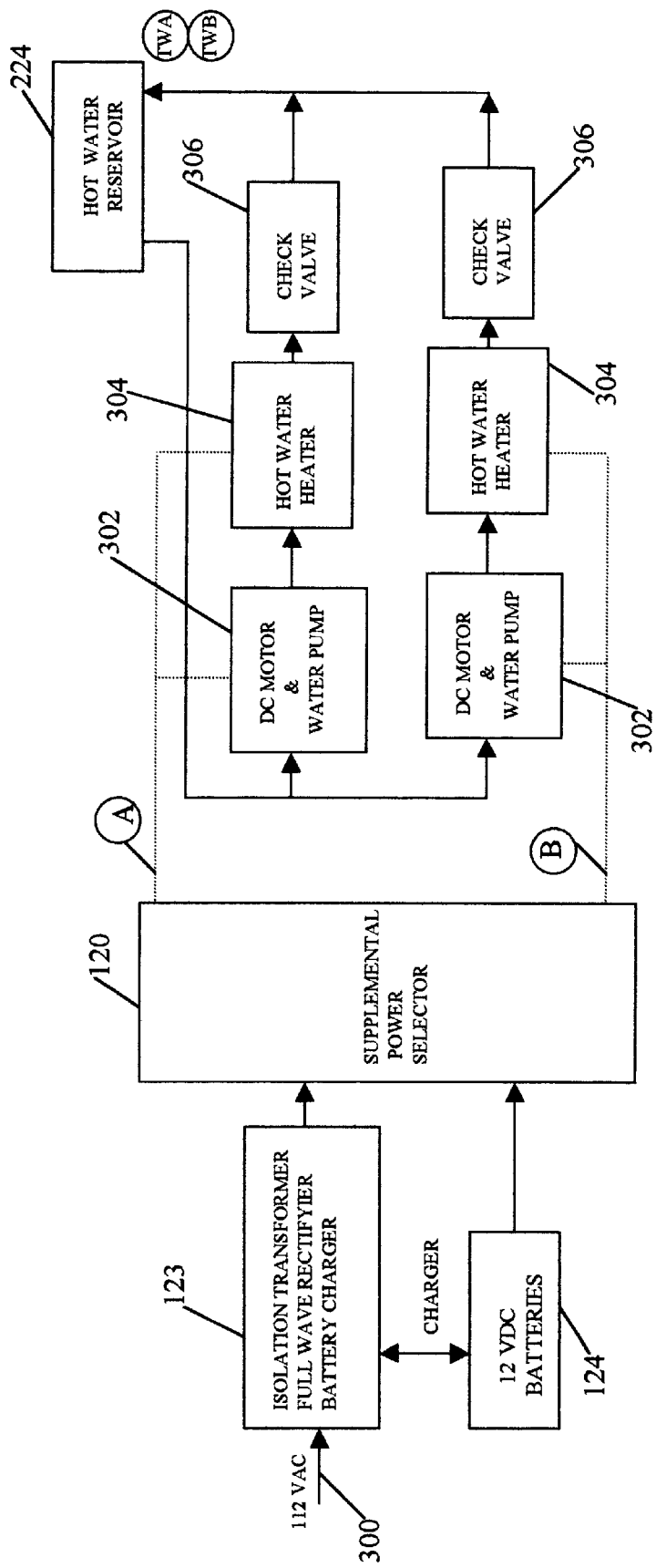
FIG. 3 is a diagrammatic view of the power supply and hot water supply to the warm water reservoir.

Referring to FIG. 3, 112 VAC 300 is supplied to an isolation transformer, full wave rectifier and battery charger combination 123, for converting AC power to DC and charging the batteries. The charging mechanism is in electrical communication with the 12 VDC batteries 124, which are in turn in electrical communication with the power management system 120, which acts as a supplemental power selector. DC motors and water pumps, generally referred to at 302, provide a flow of fluid to hot water heaters 304, which flow through check valves 306, so as to prevent reversal of flow, traverse dual temperature detectors 308 and proceed for eventual flow to warm water reservoir 224.

Figure 4:
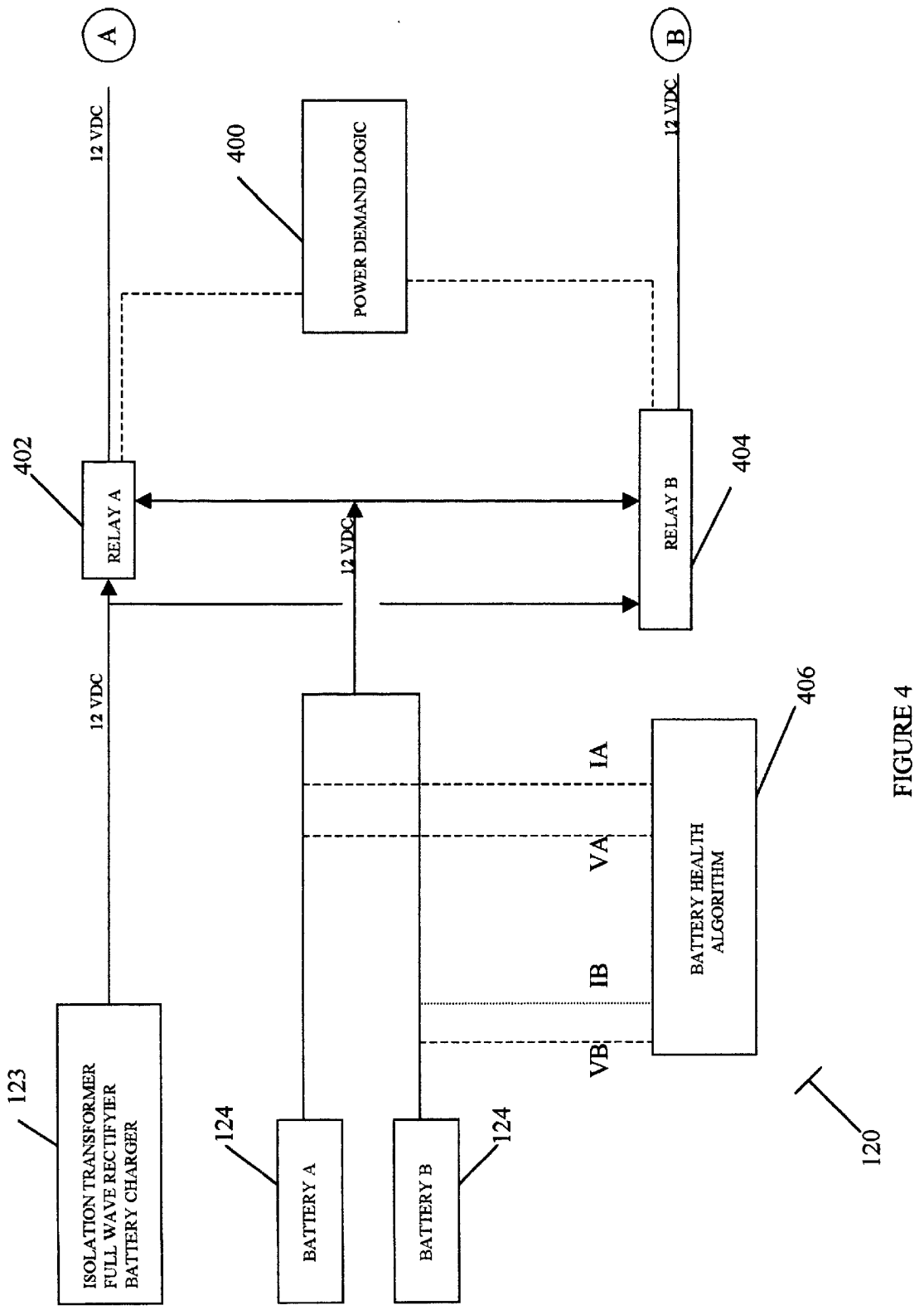
FIG. 4 is a diagrammatic representation of the supplemental power selection and battery health monitoring system.

Referring to FIG. 4, a power demand logic system 400, communicates with relays 402 and 404 to coordinate the flow of energy to the system. When sufficient energy can be supplied via the facility AC power alone, the batteries are bypassed. However, when the power required surpasses that which can be provided by the facility, then supplemental power is drawn from batteries 124 and is provided to the system. The battery condition is monitored through a device 406 which utilizes a battery health algorithm, to monitor the instantaneous battery condition, along with monitoring of the long term condition and utilization of the batteries.

Figure 5:
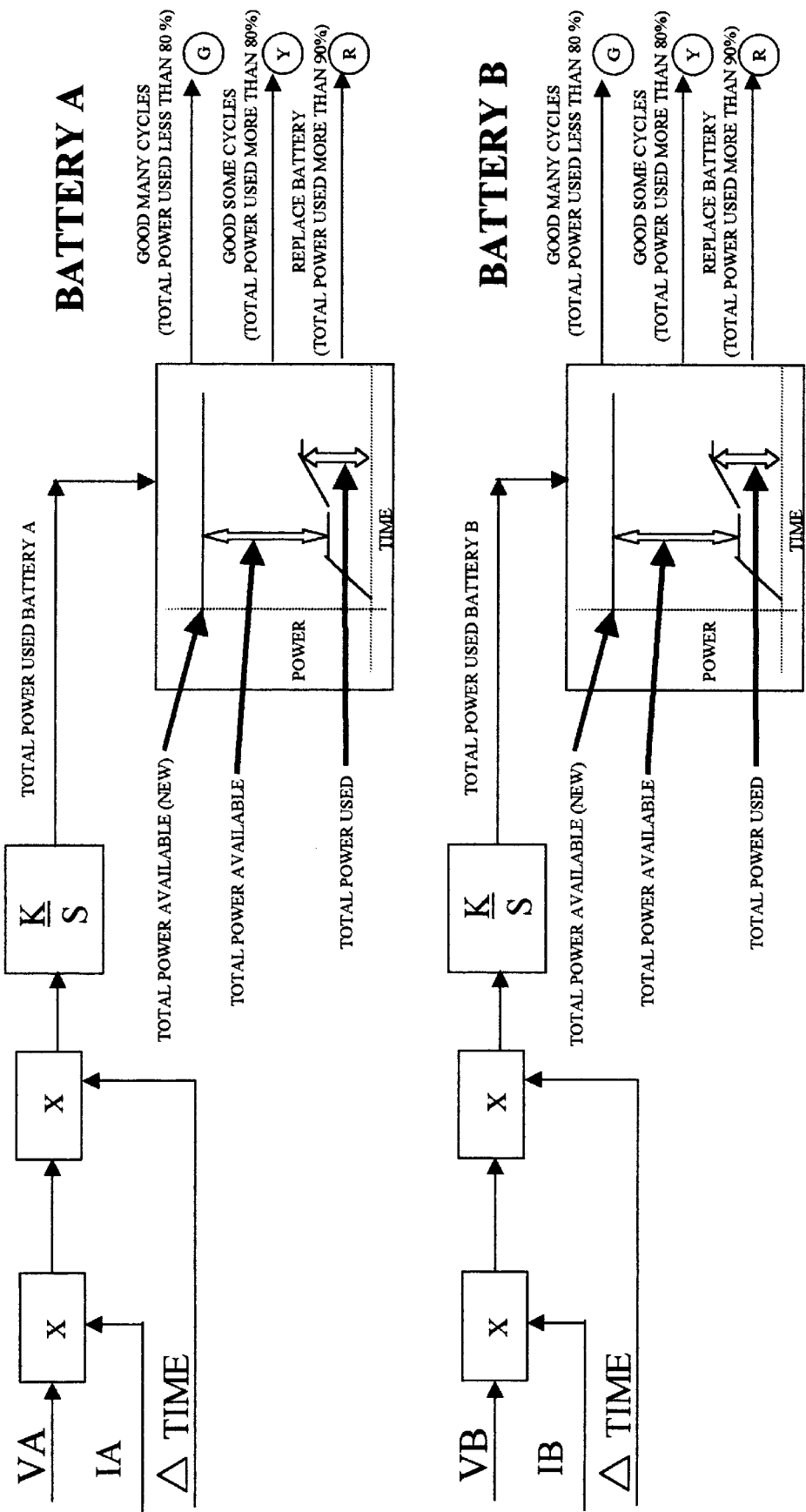
FIG. 5 is a diagram setting forth the battery health algorithm.

FIG. 5 is a diagrammatic representation of the battery health algorithm device. By monitoring the batteries utilization and number of cycles and totalizing this data over time, the algorithm can readily ascertain instantaneous battery voltage, along with the time available for system operation as a function of instantaneous battery capacity. Furthermore, since the ability of a battery to accept and deliver the full charge for which it was designed will degenerate over time, the battery health algorithm device maintains data on the number of cycles to which the battery has been subjected, and translates this into an easily monitored signal so as to indicate when the batteries should be changed out. This prevents the operator from utilizing what appears to be a "fully charged battery", i.e. one that reads nominal voltage, when, in reality, the age and cycle history of the battery will actually prevent it from delivering the number of ampere hours for which it is rated.

Figure 6:
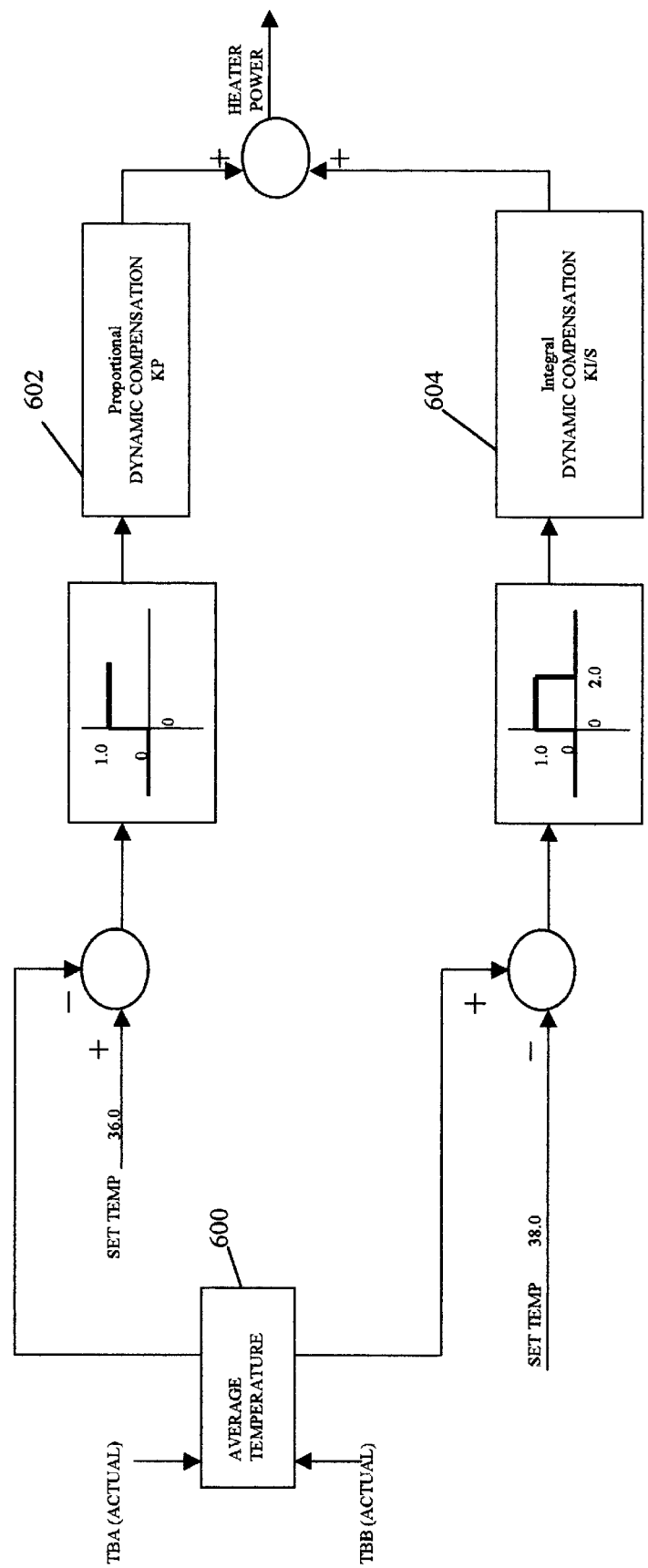
FIG. 6 describes the fluid temperature control device.

Referring to FIG. 6, the average temperature 600 of the physiological fluid is monitored via a proportional compensator circuit 602, which measures temperature up to about 36° C. Above the 36° C. set temperature, integral compensation circuit 604 is activated. Circuit 604 is able to provide a high degree of control and moderate the heater power so as to maintain a temperature of the infusate at the point of patient entry at about 38° C.+/−0.5° C., preferably +/−0.1° C.

Figure 7:
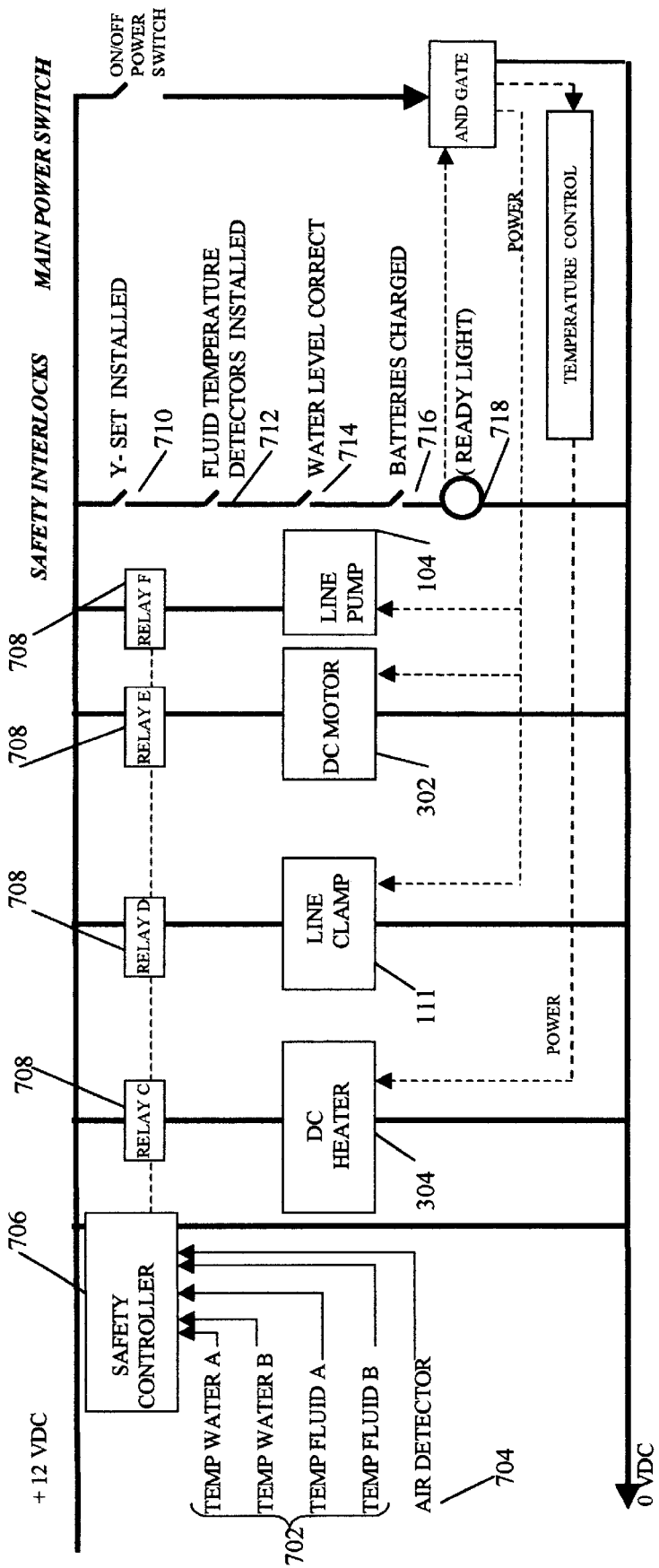
FIG. 7 describes the safety interlock system.

FIG. 7 sets forth the safety interlock system 700. Signals 702 from fluid and water temperature detectors 114 and 308 indicate primary (A) and redundant (B) temperatures for the water and physiological fluids (e.g. blood), designated as $T_{BA}$, $T_{BB}$, $T_{WA}$ and $T_{WB}$, and a signal 704 from air detector 110 provides information to the safety controller 706. These signals are communicated to relays 708 which control operation of the DC heaters 304, line clamp 111, DC motor 302 and line pump motor 104. Additional interlocks are provided to signal that the Y-set is installed 710, that the fluid temperature detector 712 is installed, that the water level is correct 714, and that the batteries are adequately charged 716. When all conditions are satisfied, the operator will be given an "READY" signal 718, and operation may begin.

Figure 8:
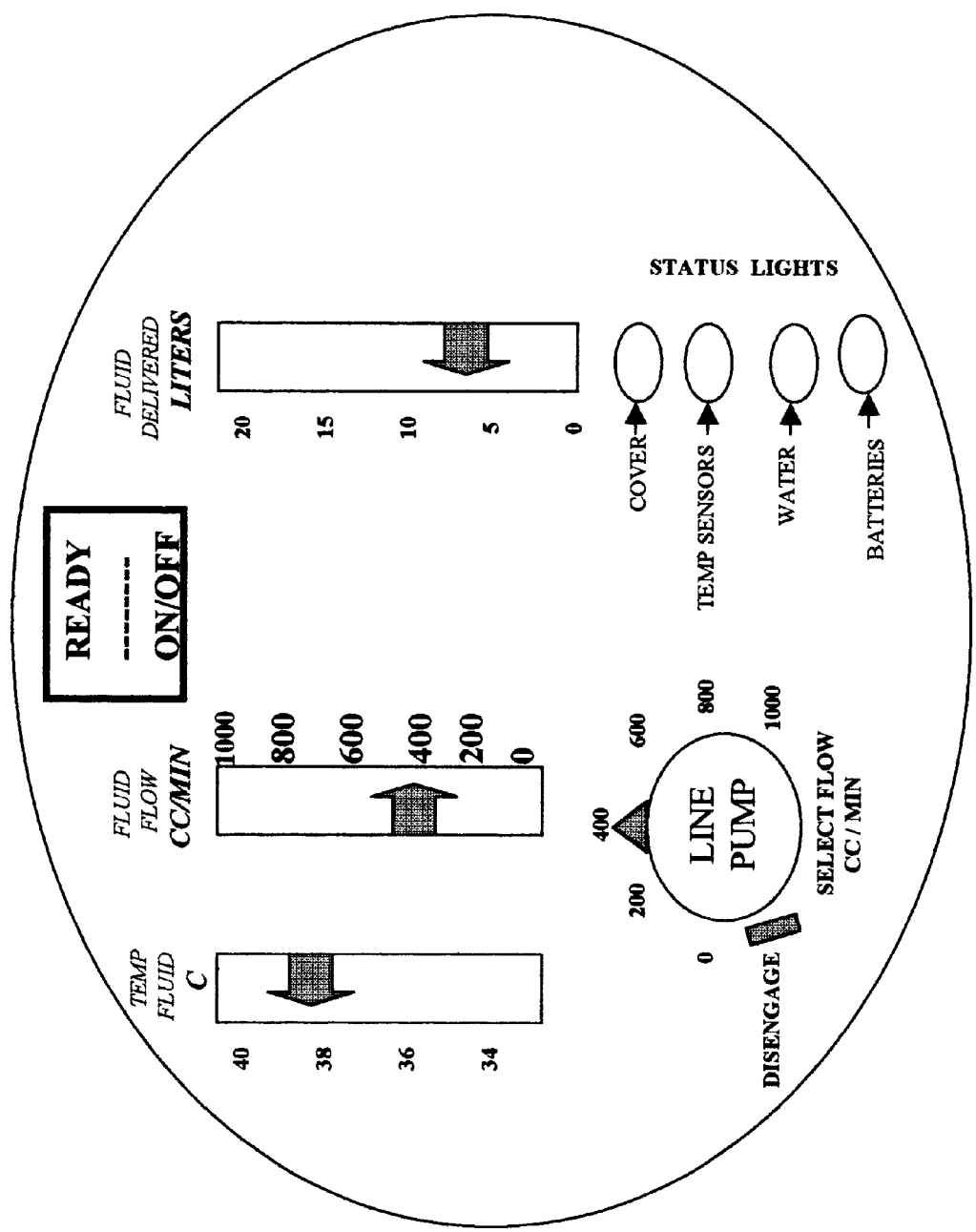
FIG. 8 illustrates the appearance of a typical cover assembly.

Referring to FIG. 8, a typical configuration for the cover top 206 is shown, wherein bar graph type indicators having an arrow pointer which moves vertically are utilized to indicate the various critical parameters as explained above, and to further indicate total volume of fluid delivered and system status.

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A warming device for a physiological fluid selected from the group consisting of crystalloids, synthetic colloids, blood products, whole blood, packed cells, plasma and mixtures thereof comprising:
   1) a warm water bath assembly including air detecting means and line clamping means;
   2) a disposable heat exchanger assembly and Y-set adapted for removable engagement and fluid coupling within said warm water bath assembly;
   3) a warm water bath assembly power management and temperature control device, characterized by a self-contained 12 volt DC power supply and a concurrent 112 volt AC power supply, constructed and arranged to provide power concurrently and in an amount effective to maintain physiological fluid temperature within nominal design parameters; and
   4) a warm water bath cover assembly containing an operator panel constructed and arranged to contain an integral line pump;
   wherein physiological fluids are delivered to a patient at a flow rate and temperature characterized as being within nominal design parameters effective to correct hypovolemic conditions while maintaining patient temperature within normothermic limits.

2. The warming device of claim 1 wherein the fluid is supplied to the patient at flow rates of up to about 1000 cc/min and at temperatures within normothermic limits, said temperatures varying about 0.5° C. between said warming device and the patient.

3. The warming device of claim 1, wherein said Y-set requires from 50–100 ml priming volume.

4. The warming device of claim 1 wherein said Y-set is characterized as containing insulated plastic tubing effective to maintain the physiological fluid at normothermic limits with a tolerance of at least about +/−0.5° C. at a flow rate of up to about 1000 cc/min.

5. The warming device of claim 1 wherein said DC power source is effective to provide up to about 500 cc/min of warmed physiological fluid in a temperature range of about 33° C. to 40.5° C. with a tolerance of at least about +/−0.5° C.

6. In combination with a warming device for physiological fluids, a power management system for integration of a 12 VDC power source and a 112 VAC power source, in combination and in response to power requirements as commanded by a temperature control assembly;
   said power management system including, in electrical communication, an isolation transformer, a full wave rectifier and a battery charging device, constructed and arranged to simultaneously provide DC power to the device in an amount effective to maintain physiological fluid temperature within nominal design parameters and providing automatic charge maintenance of the 12 VDC system.

7. In combination with a physiological fluid warming device for delivering said fluid to a patient, said warming device utilizing both AC and DC sources of electric power, a temperature control system characterized by a combination of analog and digital controllers utilizing proportional and integral control algorithms, system models and dynamic compensation to calculate AC and DC power requirements whereby said physiological fluid is infused to a patient at a temperature which is maintained within nominal design temperature parameters effective to prevent hypothermia induced shock.

8. The fluid warming device of claim 1, wherein said heat exchanger is spirally configured and contained within a housing constructed and arranged for plug-in interfacing with a centrally disposed mounting surface within a warm water reservoir; and wherein said heat exchanger is configured such that the water connections are axially aligned and are self-sealing upon assembly; said heat exchanger assembly being further characterized by integral means for physiological fluid filtration and air venting, said physiological fluid filtration and air venting means being located within the warm water reservoir whereby heat loss to the surroundings are minimized.

9. The fluid warming device in accordance with claim 1 wherein said air detection means includes an ultrasonic air detector for sensing air bubbles within the physiological fluid within a time window, which means is electronically coupled to shutoff means characterized as an electronic solenoid controlled line clamp, and wherein, upon the concentration of air bubbles exceeding a particular value, said air detection means provides a signal to the solenoid controlled clamp to prevent fluid flow to the patient.

10. The fluid warming device of claim 9 wherein the particular value of air bubble concentration should not exceed about 50–100 microliters air bubble volume.

11. A disposable Y-set and heat exchanger assembly for use in a physiological fluid warming system comprising:

tapping means for attachment to one or more vessels containing a physiological fluid to be heated, said fluid selected from the group consisting of whole blood, packed cells, plasma or mixtures thereof, said tapping means constructed and arranged to provide for a flow of liquid from said vessels and being in fluid connection with flow control means to prevent flow reversal;

an adjustable flow control valve in series connection therewith for providing volumetric flow control within the physiological fluid warming system;

a heat exchanger assembly constructed and arranged for plug-in fluid coupling with a source of warming fluid, said assembly including a reservoir for maintaining a desired volume of warming fluid and a means for providing traversal of said fluid to be heated within said reservoir, in heat exchange relationship with said warming fluid, thereby creating a warmed fluid, said assembly further including integral means for venting air and providing filtration of said warmed fluid, and insulated outlet means for directing said warmed fluid to a Y-coupling;

said Y-coupling, which is in fluid communication with said heat exchanger assembly, being fluidly connected to one or more insulated fluid conduits each of which is in fluid communication with flow control valves.

12. The disposable Y-set and heat exchanger assembly of claim 11, further including:

one or more locking connector means;

wherein each of said one or more locking connector means are removably attached to a fluid conduit which is fluidly coupled to the bloodstream of a patient.

* * * * *